US009732295B1

(12) United States Patent
Wright et al.

(10) Patent No.: US 9,732,295 B1
(45) Date of Patent: *Aug. 15, 2017

(54) DIESEL AND JET FUELS BASED ON THE OLIGOMERIZATION OF BUTENE

(71) Applicant: The United States of America, as Represented by the Secretary of the Navy, Washington, DC (US)

(72) Inventors: Michael E Wright, Tremonton, UT (US); Benjamin G Harvey, Ridgecrest, CA (US); Roxanne L Quintana, Ridgecrest, CA (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 21 days.

This patent is subject to a terminal disclaimer.

(21) Appl. No.: 14/872,418

(22) Filed: Oct. 1, 2015

Related U.S. Application Data

(60) Division of application No. 13/763,829, filed on Feb. 11, 2013, now Pat. No. 9,181,144, which is a continuation-in-part of application No. 12/511,796, filed on Jul. 29, 2009, now Pat. No. 8,395,007.

(51) Int. Cl.
| | | |
|---|---|---|
| *C10L 1/04* | (2006.01) | |
| *C10L 1/00* | (2006.01) | |
| *C07C 9/12* | (2006.01) | |
| *C07C 9/00* | (2006.01) | |
| *C10L 1/08* | (2006.01) | |

(52) U.S. Cl.
CPC ........ *C10L 1/08* (2013.01); *C10L 1/04* (2013.01); *C10L 2200/0469* (2013.01); *C10L 2270/026* (2013.01); *C10L 2270/04* (2013.01); *C10L 2290/543* (2013.01)

(58) Field of Classification Search
CPC ........ C10L 1/08; C10L 1/04; C10L 2290/543; C10L 2270/026; C10L 2270/04; C10L 2200/0469
See application file for complete search history.

(56) References Cited

U.S. PATENT DOCUMENTS

| | | | |
|---|---|---|---|
| 4,165,301 | A | 8/1979 | Wiegers et al. |
| 4,209,653 | A | 6/1980 | Sato et al. |
| 4,410,749 | A | 10/1983 | Burdette |
| 4,658,078 | A | 4/1987 | Slaugh et al. |
| 4,720,600 | A | 1/1988 | Beech et al. |
| 4,791,180 | A | 12/1988 | Turner |
| 4,922,047 | A | 5/1990 | Chen et al. |
| 5,723,709 | A | 3/1998 | Phillips, Jr. et al. |

(Continued)

OTHER PUBLICATIONS

"Highly Efficient Zirconium Catalyzed Batch Conversion of 1-Butene: A new route to Jet Fuels", Energy & Fuels (2008) 22, 3299-3302 (Published online Jul. 29, 2008) by Michael E Wright, Benjamin G Harvey and Roxanne L Quintana.*

*Primary Examiner* — Pamela H Weiss
(74) *Attorney, Agent, or Firm* — Charlene A. Haley

(57) ABSTRACT

A renewable biofuel based on a highly efficient batch catalysis methodology for conversion of 1-butene to a new class of potential jet fuel blends. By tuning the catalyst and then using the dimer produced, the carbon use is about 95% or greater. This latter point will be particularly important in the future, where the source of raw materials (i.e., biomass/biofeedstock) is limited.

14 Claims, 6 Drawing Sheets

(56) References Cited

U.S. PATENT DOCUMENTS

| | | | |
|---|---|---|---|
| 5,847,247 A | 12/1998 | Conte et al. | |
| 6,548,723 B2 | 4/2003 | Bagheri et al. | |
| 6,828,283 B2 | 12/2004 | Chapaton et al. | |
| 7,390,397 B2 | 6/2008 | Lamprecht et al. | |
| 8,395,007 B2 * | 3/2013 | Wright | B01J 31/189 585/14 |
| 8,785,702 B2 | 7/2014 | Wright et al. | |
| 8,912,373 B2 * | 12/2014 | Wright | B01J 37/06 585/16 |
| 8,969,636 B2 * | 3/2015 | Wright | B01J 31/143 585/14 |
| 2003/0125595 A1 * | 7/2003 | Bagheri | C07C 2/34 585/520 |
| 2006/0138022 A1 | 6/2006 | Miller et al. | |
| 2006/0199984 A1 | 9/2006 | Kuechler et al. | |
| 2007/0043248 A1 | 2/2007 | Wu et al. | |
| 2008/0015395 A1 | 1/2008 | D'Amore et al. | |
| 2009/0299109 A1 | 12/2009 | Gruber et al. | |
| 2012/0271089 A1 | 10/2012 | Wright et al. | |
| 2015/0025288 A1 | 1/2015 | Wright et al. | |

\* cited by examiner

Figure 3. 1H NMR spectrum of butene oligomers
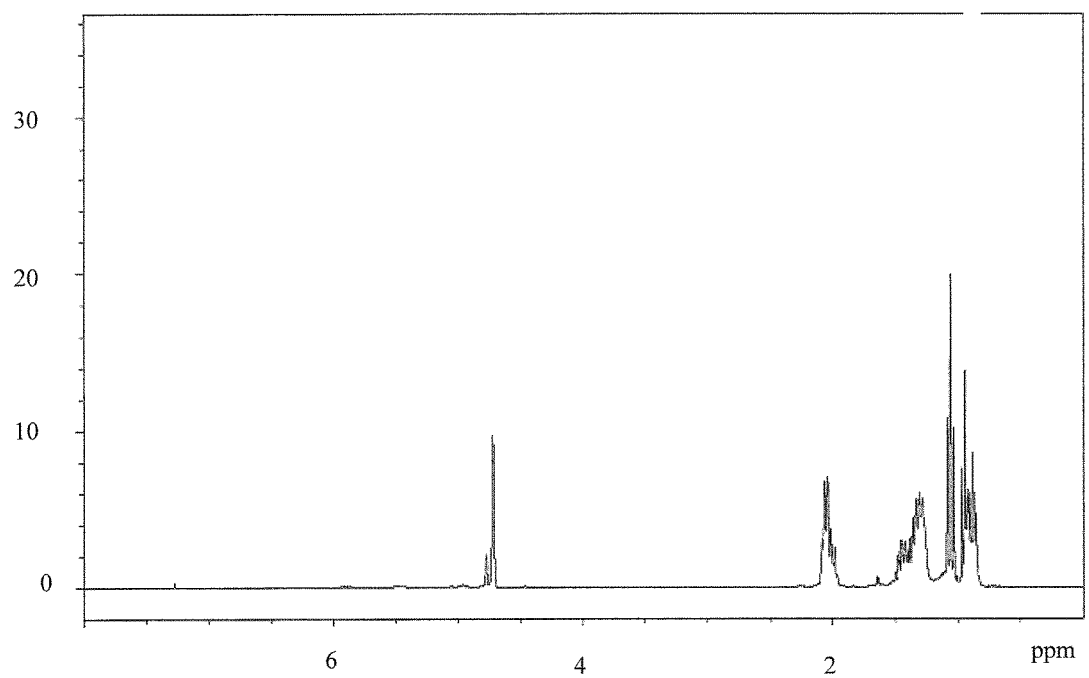

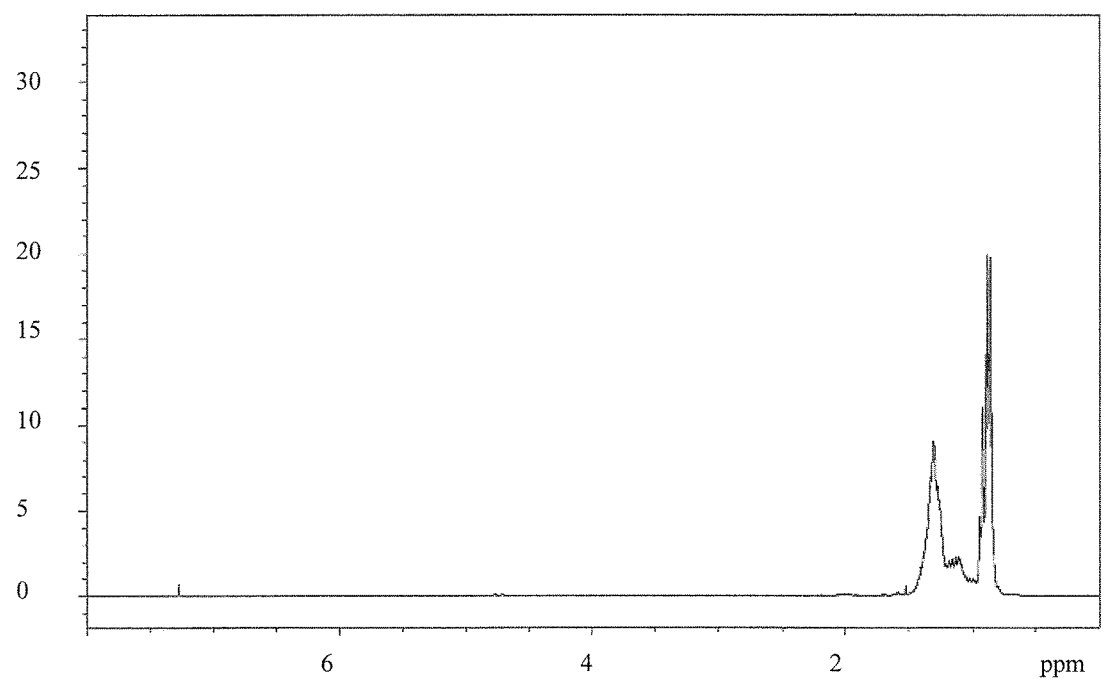
Figure 4. 1H NMR spectrum of hydrogentated butene oligomers.

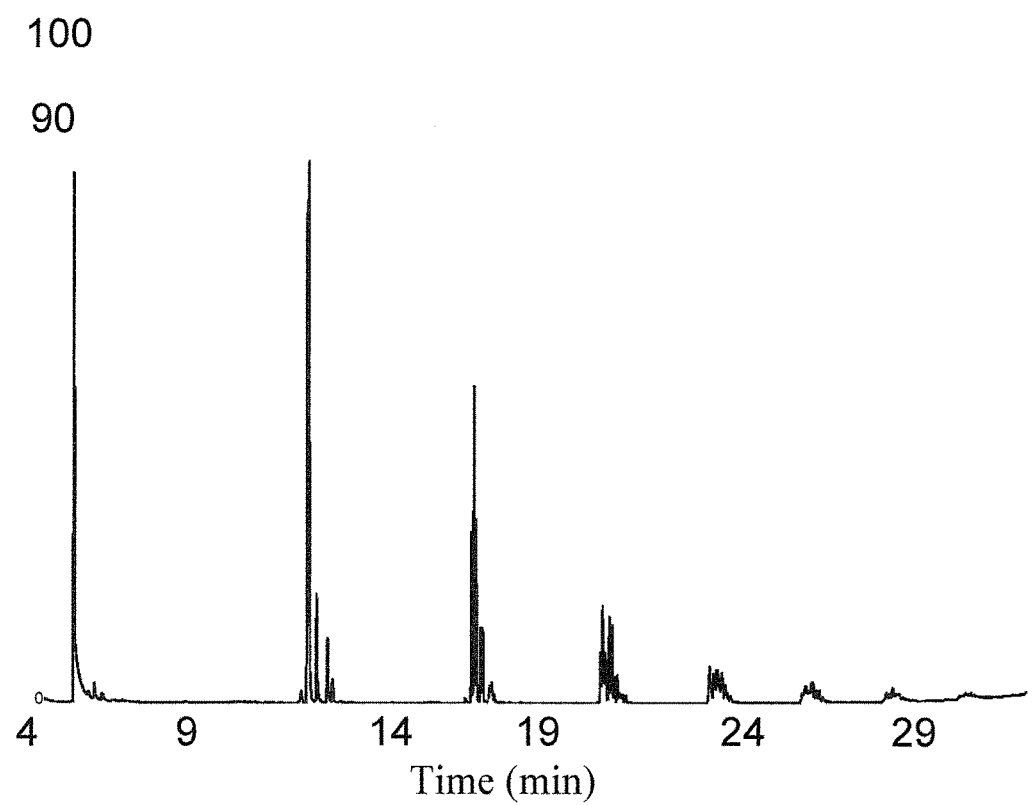
Figure 5. Gas Chromatogram of hydrogenated butene oligomers

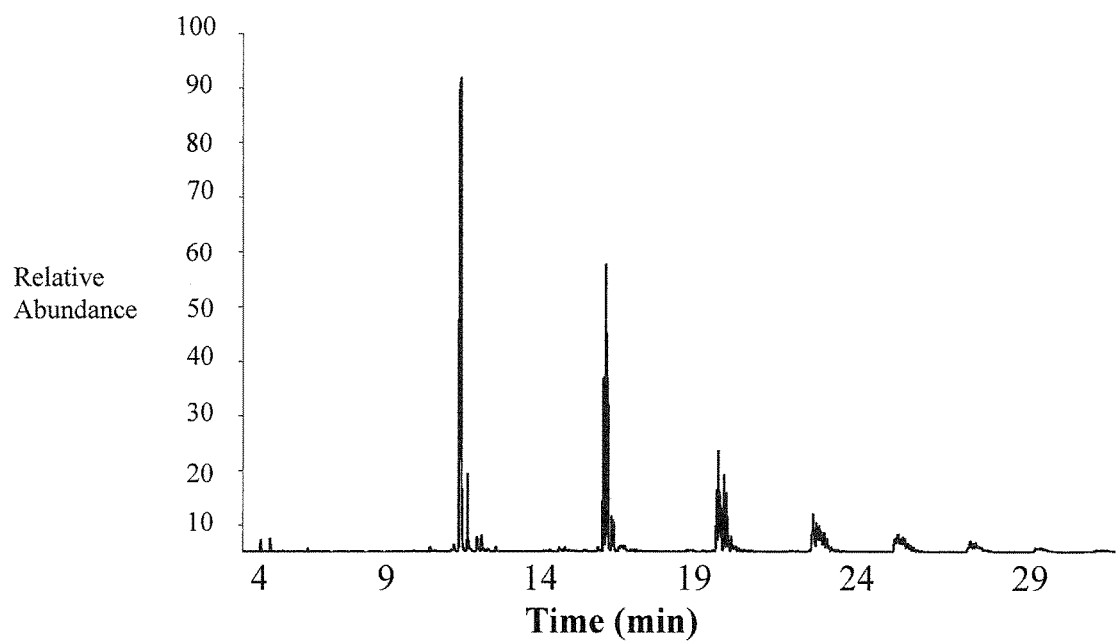
Figure 6. Gas Chromatogram of distilled fuel

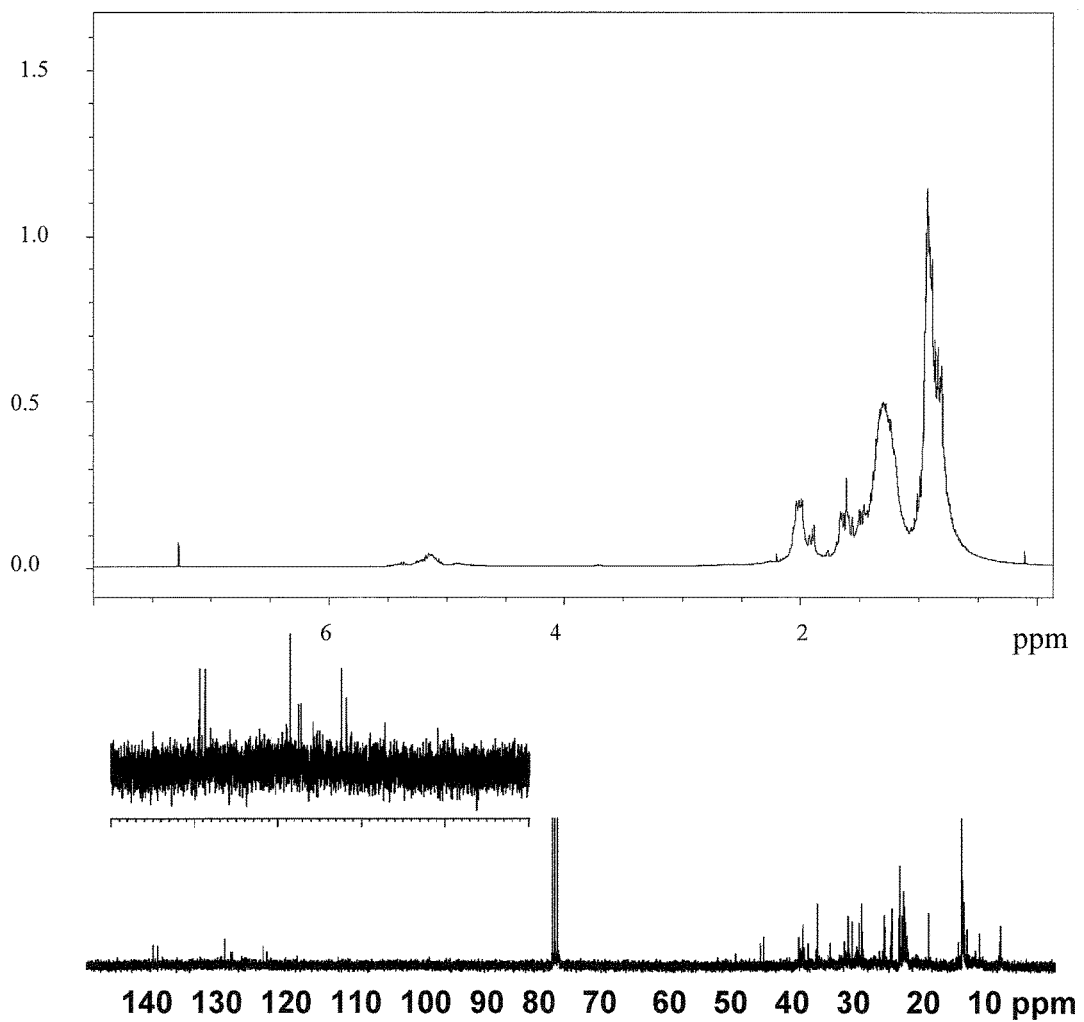
Figure 7. ¹H(top) and ¹³C (bottom) NMR spectra of the product mixture from sulfuric acid dimerization of 2-ethyl-1-hexene.

DIESEL AND JET FUELS BASED ON THE OLIGOMERIZATION OF BUTENE

CROSS-REFERENCE TO RELATED APPLICATION

This is a divisional patent application, claiming the benefit of a continuation-in-part patent application Ser. No. 13/763,829 filed on Feb. 11, 2013, which claims the benefit of, parent application Ser. No. 12/511,796 filed on Jul. 29, 2009, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

A renewable biofuel for turbine engines based on a highly efficient batch catalysis methodology for conversion of 1-butene to a new class of fuels.

BACKGROUND OF THE INVENTION

We demonstrate that the quantitative conversion of 1-butene to a Schultz-Flory distribution of oligomers has been accomplished by use of Group 4 transition-metal catalysts in the presence of methylaluminoxane (MAO). The oligomerization reaction was carried out at ambient temperature in a sealed reaction vessel with complete conversion of 1-butene at catalyst turnover numbers greater than 17,000. The combination of high catalyst activity without concomitant production of high polymer led to a highly efficient production of new hydrocarbon jet fuel candidates. The reaction proceeds with high regioselectivity; however, because achiral catalysts were used, several diastereoisomeric structures were produced and observed in the gas chromatography-mass spectrometry (GC-MS) chromatograms. The single and specific dimer formed in the reaction, 2-ethyl-1-hexene, was easily removed by distillation and then was itself dimerized using acid catalysis to yield a mixture of mono-unsaturated $C_{16}$ compounds. Changes in the oligomerization catalyst led to production of fuels with excellent cold-flow viscosity without the need for a high-temperature distillation. Thus, removal of the dimer followed by catalytic hydrogenation ($PtO_2$) led to a 100% saturated hydrocarbon fuel with a density of 0.78 g/mL, a viscosity of 12.5 cSt at −20° C. (ASTM 445), and a calculated heat of combustion of 44+MJ/kg. By back-addition of hydrogenated dimer in varying amounts (6.6, 11.5, and 17 wt %), it is possible to tailor the viscosity of the fuel (8.5, 7, and 6.5 cSt, respectively).

There exist several commercial and research programs around the world aimed at creating full-performance jet fuels based on alternative feedstocks. Traditionally, jet propulsion (JP) fuels contain a complicated array of saturated and aromatic hydrocarbons that are highly refined to meet fuel specifications for a particular application. For instance, the Navy's JP-5 has a significantly higher flash point (60° C.) in comparison to the Air Force JP-8 and commercial jet fuel (about 38° C.). (Corporan, E.; DeWitt, M. J.; Belovich, V.; Pawlik, R.; Lynch, A. C.; Gord, J. R.; Meyer, T. R. *Energy Fuels* 2007, 21, 2615-2626) (Chang, P. H.; Colbert, J. E.; Hardy, D. R.; Leonard, J. T. *Prepr. Pap. Am Chem. Soc., Div. Pet. Chem.* 2004, 49, 414). Syntroleum and Sasol have independently produced JP-5 and JP-8 equivalents based on gas-to-liquid (GTL) Fischer-Tropsch processes. (Freeks, R. L.; Muzzell, P. A. *Prepr. Pap. Am Chem. Soc., Div. Pet. Chem* 2004, 49, 407-410) (Muzzell, P. A.; Feerks, R. L.; Baltrus, J. P.; Link, D. D. *Prepr. Pap. Am Chem. Soc., Div. Pet. Chem.* 2004, 49, 411-413) and (Lamprecht, D. *Energy Fuels* 2007, 21, 1448-1453). One of the most challenging aspects to making a jet fuel using Fischer-Tropsch chemistry (Fischer, F.; Tropsch, H. *Brennst. Chem.* 1923, 4, 276) has been to meet the required coldflow properties. To date, this has required significant postprocessing or "reforming" of the fuel to increase the iso/normal paraffin product ratio. Typically, the Chevron isocracking technology produces a predominance of methyl branching at the 2 position of a hydrocarbon chain; however, the chemical product distribution is quite complicated.

Conversion of propene and butylenes to dimers/oligomers was one of the first commercial processes in the petroleum industry. (Schmerling, L.; Ipatieff, V. N. *Adv. Catal.* 1950, 21, 2). Some more recent approaches have looked at using mesoporous catalysts and newly designed large-pore acidic zeolite catalysts. (Catani, R.; Mandreoli, M.; Rossini, S.; Vaccari, A. *Catal. Today* 2002, 75, 125-131) (Schmidt, R.; Welch, M. B.; Randolph, B. B. *Energy Fuels* 2008, 22 (2), 1148-1155). Transition-metal catalysts (homo- and heterogeneous), generally grouped into the category of Ziegler-Natta (ZN), have enjoyed a successful history for converting olefins, in particular, ethylene and propene, into oligomeric and polymeric materials. (Natta, G. *J. Polym. Sci.* 1955, 16, 143) (Natta, G.; Pino, P.; Corradti, P.; Danusso, F.; Mantica, E.; Mazzanti, G.; Moraglio, G. *J. Am. Chem. Soc.* 1955, 77, 1708) (Natta, G. *Angew. Chem.* 1956, 12, 393. Ziegler, K. *Angew. Chem.* 1952, 64, 323) (Ziegler, K.; Holzkamp, E.; Breil, H.; Martin, H. *Angew. Chem.* 1955, 67, 541) (Janiak, C. *Coord. Chem. ReV.* 2006, 250, 66-94) (Belov, G. P. *Petrol. Chem.* 1994, 34, 105). Studies using 1-butene can involve a co-polymerization reaction with more reactive olefins, such as ethylene or propene. (Janiak, C.; Blank, F. *Macromol. Symp.* 2006, 236, 14-22). A study by Kaminsky explored the oligomerization of 1-butene using selected chiral Group 4 transition-metal catalysts and methylaluminoxane (MAO). (Kaminsky, W. *Macromol. Symp.* 1995, 89, 203-219). In general, the catalysts studied required elevated reaction temperatures and typically led to incomplete conversion of the 1-butene. A study by Christoffers and Bergman reported that using an aluminum/zirconium ratio of 1/1 and with a nearly stoichiometric amount of zirconium "catalyst" that 1-butene could be converted selectively to dimer (2-ethyl-1-hexene). (Christoffers, J.; Bergman, R. G. *Inorg. Chim. Acta* 1998, 270, 20).

In undertaking this research our goal was to create a full-performance JP-5/tactical biojet fuel that can be derived from a fully renewable and sustainable source of reduced carbon. Carbon dioxide is initially reduced via photosynthesis (e.g., cellulose and triglyceride oils). Further reduction can occur in a second fermentation or microbial treatment to afford an alternative biofuel and/or biofeedstock. (Wright, M. E.; Harvey, B. G.; Quintana, R. *Prepr. Pap. Am. Chem. Soc., Fuel Div.* 2008, 53 (1), 252-253.)

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments which are illustrated schematically in the accompanying drawings and in the appended claims.

BRIEF DESCRIPTION OF THE DRAWINGS

FIG. 3 of the drawings is an $^1$H NMR spectrum of butene oligomers.

FIG. 4 of the drawings is an $^1$H NMR spectrum of hydrogentated butene oligomers.

FIG. 5 of the drawings is a Gas Chromatogram of hydrogenated butene oligomers.

FIG. 6 of the drawings is a Gas Chromatogram of distilled fuel.

FIG. 7 of the drawings is a $^1$H (top) and $^{13}$C (bottom) NMR spectra of the product mixture from sulfuric acid dimerization of 2-ethyl-1-hexene.

Figure 1:
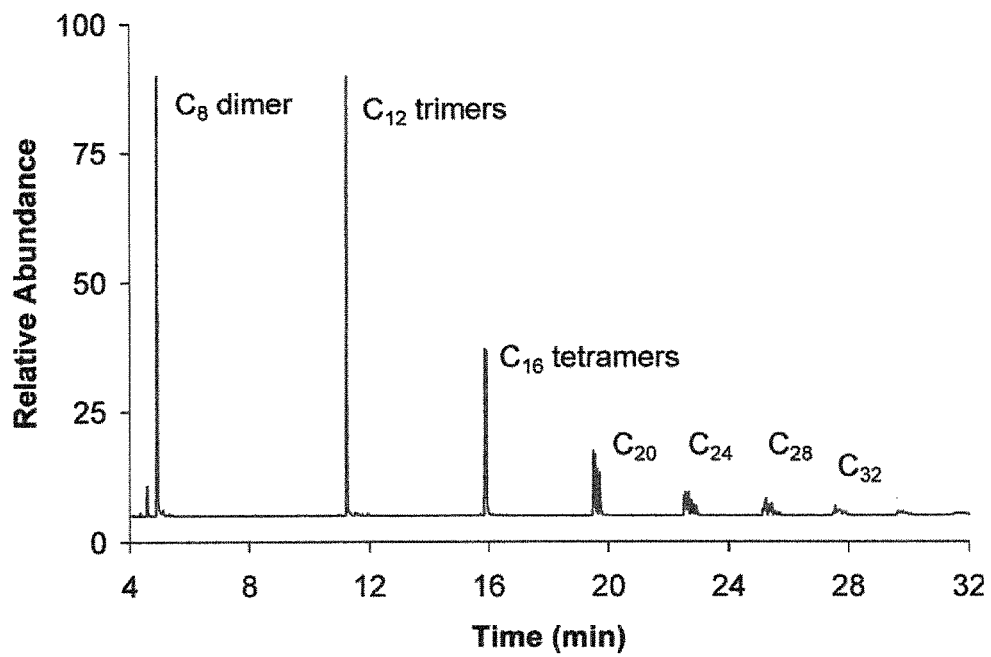
FIG. 1 of the drawings is a plot of GC-MS total ion chromatogram for the oligomers produced from 1-butene.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

DETAILED DESCRIPTION OF THE INVENTION

Given recent advances in the conversion of starch (Ramey, D. E. U.S. Pat. No. 5,753,474) and cellulosic biomass to biobutanol (Qureshi, N.; Sahaa, B. C.; Hector, R. E.; Hughes, S. R.; Cotta, M. A. *Biomass Bioenergy* 2008, 32 (2), 168-175. Qureshi, N.; Sahaa, B. C.; Cotta, M. A. *Biomass Bioenergy* 2008, 32 (2), 176-183), we explored using the C4 alcohol as a pivotal and versatile starting point for the creation of new fuels. Because both butyl ether and 1-butene can be easily derived from 1-butanol (Berteau, P.; Delmon, B.; Dallons, J. L.; Vangysel, A. *Appl. Catal.* 1991, 70 (2), 307-323. Bautista, F. M.; Delmon, B. *Appl. Catal., A* 1995, 130 (1), 47-65), we investigated use of these chemicals as precursors to biojet fuels that will meet the required energy content and key performance specifications of JP-5 jet fuel. We disclose here methods for converting 1-butene into a variety of useful saturated hydrocarbon fuels using a highly efficient batch-catalysis process. The new approach affords a product that is composed of 100% iso-paraffins, retains good fuel density, possesses attractive cold-flow properties, and can be easily tailored to have a high flash point.

We initiated our synthetic fuel experiments using the commercially available precatalyst bis(cyclopentadienyl) zirconium dichloride. The precatalyst is activated by treatment with a toluene solution of MAO followed by removal of the toluene under reduced pressure. The MAO may also be prepared in a solution of any aromatic solvent able to solvate the MAO and the precatalyst such as, without limitation, for example xylene, cumene, and mesitylene. Of course, coordinating solvents with heteroatoms are not appropriate. Removal of solvent after catalyst activation also removes any residual trimethylaluminum, creating "dried" MAO. The "dried" MAO has been shown to have a significant affect on catalyst activity for olefin oligomerization/polymerization reactions for several non-metallocene catalysts. (Hasan, T.; Ioku, A.; Nishii, K.; Shiono, T.; Ikeda, T. *Macromolecules* 2001, 34 (10), 3142-3145) (Hagimoto, H.; Shiono, T.; Ikeda, T. *Macromol. Rapid Commun.* 2002, 23, 73) (Furayama, R.; Saito, J.; Ishii, S.; Mitani, M.; Matsui, S.; Tohi, Y.; Makio, H.; Matsukawa, N.; Tanaka, H.; Fujita, T. *J. Mol. Catal. A: Chem.* 2003, 200, 31) (Long, R. J.; Gibson, V. C.; White, A. J. P. *Organometallics* 2008, 27 (2), 235-245). We have consistently prepared our catalyst using an aluminum/zirconium ratio of 100 (mol/mol). It may be noted that here the MAO is an oligomer of formula $[CH_3AlO]_n$ and there is one mole of aluminum for every mole of MAO repeat unit. Similarly, there is one mole of Zr per mole of $Cp_2ZrCl_2$. Conveniently, both the molar ratio of MAO/$Cp_2ZrCl_2$ and Al/Zr is 100:1. We point out as well, that the turnover number (TON) here is at least about 17,000 and may be pushed to as high as on the order of $10^7$ whereas the TON utilized by Christoffers and Berg was only about 10 or less. It is well known that use of very high Al/M ratios on the order of 10,000:1 results in the production of polymers, whereas significantly lower ratios leads to oligomeric mixtures. Our use of the Al/M ratio 100:1 is an approximate first optimization of the system based upon previous observations.

The 1-butene (375 mL, about 240 g) is condensed onto $CaH_2$ and then transferred over the course of 3 h to a chilled (dry ice bath) pressure reaction vessel containing "activated" catalyst. Reactions were performed in a Parr steel pressure reaction vessel lined with a glass insert and stirring was accomplished using a Teflon coated stirring bar. The 1-butene [Specialty Gas Concepts, Lancaster, Calif., 98% Chemically Pure (CP) grade] was transferred after drying (over $CaH_2$) to the chilled reaction vessel through Tygon tubing. Once the pressure vessel was charged, the port was sealed, the cooling bath was removed, and the reaction was run for 16 h. The reaction vessel is sealed and allowed to react with stirring at ambient temperature for 16 h (Scheme 1). At completion of the reaction, a partial vacuum exists in the reaction vessel. This observation is consistent with complete consumption of the 1-butene (bp −6.3° C.). Gas chromatography-mass spectrometry (GC-MS) analysis indicates a Schultz-Flory distribution of products consisting primarily of C8, C12, and C16 oligomers with small amounts of heavier oligomers. GC-MS analyses were performed using an Agilent 6890 gas chromatography (GC) system equipped with a Restek RTX-5MS 30 m column coupled to an Agilent 5973 mass selective detector system. After quenching as described herein below, a distillation using a vigreux column is used to remove the $C_8$ dimer, which accounts for about 25 wt % of the product mixture. Roughly 90% of the butene oligomer mixture consists of $C_8$ dimer and $C_{12}$, $C_{16}$, $C_{20}$, and $C_{24}$ oligomers, and there are essentially no oligomers larger than $C_{32}$. After removing the $C_8$ dimer, hydrogenation (about 0.08 wt % $PtO_2/H_2$, 2 psig) of the remaining oligomers yields a potential diesel fuel that has a flash point (ASTM D93) of 59° C., viscosity of 103 cSt (ASTM D445 at −20° C.), and a lubricity value of 0.45 mm [ASTM 6079, high frequency reciprocating rig (HFRR)]. All ASTM tests herein were performed at the Southwest Research Institute, San Antonio, Tex. 78238 (www.swri.org). Interestingly, this fuel does not show any sign of freezing (or cloudiness) when cooled to −60° C. When this fuel blend is subjected to a second high-temperature distillation, a colorless viscous oil residue is left behind that accounts for about 11% of the total fuel production. It is this oil fraction that leads to the good lubricity value for the fuel.

It is important to note that incremental jumps are made in 4-carbon units, the reaction is highly regioselective based on GC-MS data, and the fuels generated in this process are 100% iso-paraffinic. The branching is quite distinctive in that ethyl groups are located at regular positions along the carbon main chain of the oligomer. Furthermore, not only does this fuel have extensive branching, it contains a mixture of diastereoisomers that are produced as a consequence of the chiral carbon centers (marked with an asterisk in Scheme 1) generated at the branch points. The diastereoisomers have different physical properties (e.g., boiling point) and can be clearly observed in both the nuclear magnetic resonance (NMR) spectra and GC-MS chromatograms. For example, the hydrogenated tetramer has three chiral centers. Using the standard formula of 2n (where n is the number of chiral centers) will have 8 possible stereoisomers. This consists of 4 pairs of enantiomers and 4 different diastereoisomers.

Hence, after hydrogenation of the trimer and generation of a second chiral center, two major peaks in the GC-MS chromatogram are observed. This observation is consistent with the structures shown in Scheme 1 and the regiochemistry anticipated from the earlier work of Kaminsky (above) on the ZN-catalyzed reactions of 1-butene.

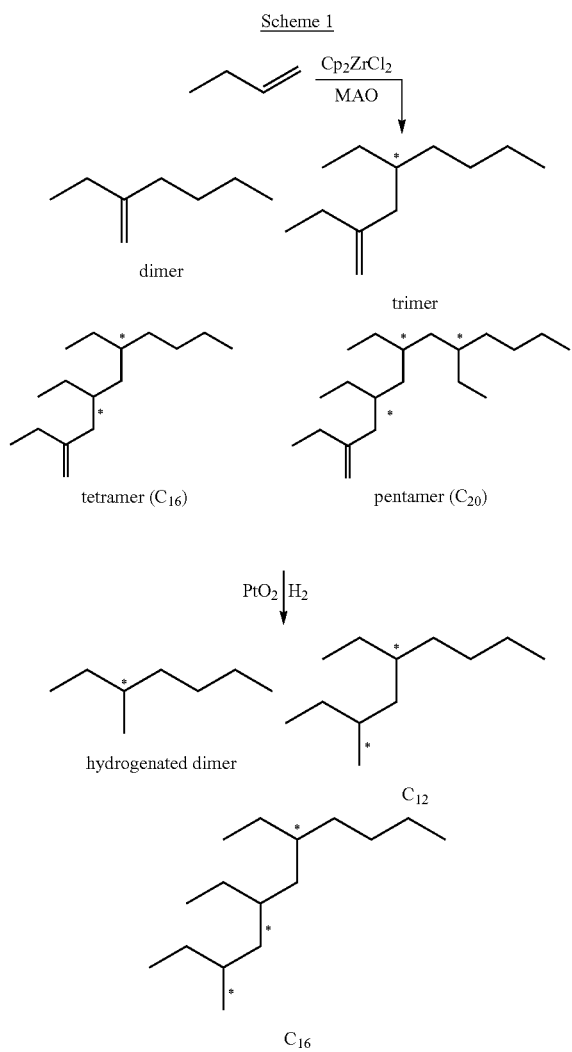

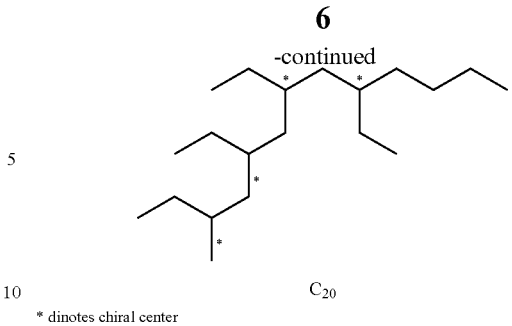

* dinotes chiral center

Figure 2:
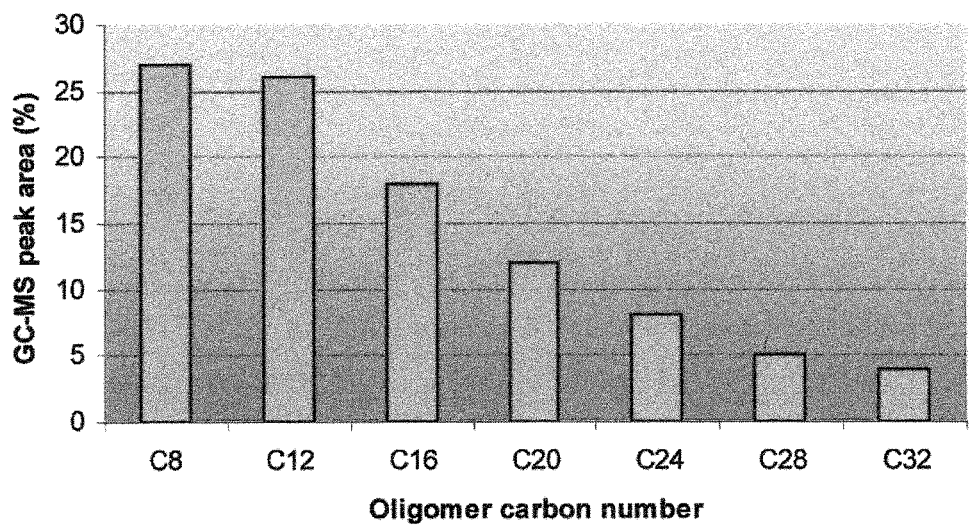
FIG. 2 of the drawings is a graph of relative area integration for each of the oligomers by carbon number for the GC-MS chromatogram of FIG. 1 above.

By making a change in catalyst preparation, we are able to produce a significant change in the resulting oligomer distribution toward lighter oligomers; however and importantly, the complete, or near complete, conversion of 1-butene remains unchanged. The catalyst is first formed in solution, then dried under vacuum and suspended in a small volume of hydrogenated butene dimer (3-methyl-heptane) derived from a previous run. This allows for reaction in which the solvent is primarily the reactant, 1-butene, without the need for addition of other solvent. This approach results in a mostly heterogeneous catalyst (i.e., the catalyst is dispersed in the solvent, but is not in solution, or is present in solution in only very low concentration). Using this heterogeneous, unsupported catalyst in the reaction results in a remarkable product distribution consisting primarily of dimer, trimer, and tetramer, but without production of heavy oligomers and polymer. This metallocene based unsupported heterogeneous catalyst method is a novel approach that results in a unique product distribution. Thus, we have discovered that if, after removal of the toluene, the aluminum/zirconium catalyst is slurried in hydrogenated dimer and then delivered to the reactor, the surprising result is: (1) complete, or essentially complete, conversion of 1-butene to oligomers as evidenced by a partial vacuum after completion of the reaction and the yield of oligomers obtained from the initial reactants; (2) an about 12 wt % increase in 2-ethyl-1-hexene dimer produced; and, (3) a decrease of high-molecular-weight oligomer generated, with the distribution defined by Mn) 176, Mw) 211, and Mw/Mn) 1.2, where, Mn is number average molecular weight, Mw is weight average molecular weight, and Mw/Mn is the polydispersity (FIG. 1). This distribution can be observed in FIG. 1 which is a plot of a GC-MS total ion chromatogram for the oligomers produced from 1-butene (Al/Zr: 100) using the catalyst made by removal of the toluene and delivering the zirconium/MAO as a slurry in hydrogenated dimer (3-methyl heptane). It will be understood by one of ordinary skill in the art that any lower molecular weight $C_4$ to about $C_{10}$ alkane may be used in place of 3-methy-heptane, such as for example, butane, pentane, hexane, heptane, octane, and branched chain alkanes. FIG. 2 is a relative area integration for each of the oligomers by carbon number for the GC-MS chromatogram of FIG. 1. The relative abundance areas are derived from the total ion count for the peaks of that particular set of oligomers (e.g., $C_{24}$). We typically obtain yields of 98% or more with some loss of product due to filtration, handling and transfer. This advantageously also enables the entire procedure to be performed using simple Schlenk techniques while avoiding using a glovebox. At this time, we do not completely understand the exact chemical differences/changes in the new active catalyst; however, the results are very consistent from run to run for this new catalyst preparation. As before, distillation is used to remove the 2-ethyl-1-hexene dimer, and the resulting fuel blend of oligomers minus the dimer is subjected to hydrogenation. Using the new catalyst formulation, we observe a significant decrease in viscosity, down to 12.5 cSt, (entry 1 in Table 1) compared to products prepared using our earlier catalyst formulation. We can further tailor the cold-flow viscosity by back-addition of hydrogenated $C_8$ dimer. Thus, by adding 6.6 wt % (entry 2 in Table 1) of the dimer, the viscosity decreases to 8.5 cSt, which is quite close to JP-8 (8.0 cSt) and does meet the JP-5 (8.5 cSt) specification.

TABLE 1

Viscosity Data (ASTM D445, −20° C.) for Fuel Blendsα

| fuel blend | viscosity (cSt) | dimer (%) | fuel density (g/mL) |
|---|---|---|---|
| 1 | 12.5 | 0 | 0.78 |
| 2 | 8.5 | 6.6 | 0.77 |
| 3 | 7.2 | 11.5 | 0.77 |
| 4 | 6.0 | 17 | 0.76 |

αCatalyst delivered as a slurry in hydrogenated dimer.

Further dilution with the $C_8$ dimer brings the viscosity down to an impressive 6.0 cSt at −20° C. (entry 4 in Table 1). As anticipated, there is a decrease in fuel density as the dimer concentration increases. Carrying out a high-temperature distillation to 313° C. leaves a colorless pot residue of less than 1 wt % and physically/experimentally confirms the decrease in high-molecular-weight oligomer content. For the fuel blend of entry 1 in Table 1, elemental analysis indicates 85% carbon and 15 wt % hydrogen, which is consistent with a fully saturated hydrocarbon. It follows that the calculated heat of combustion is greater than 44+MJ/kg or 34.3+MJ/L. The heat of combustion is calculated for the stoichiometric reaction with oxygen to form carbon dioxide and water using an average formula of $C_{16}H_{34}$. The elemental analysis was performed at Atlantic Microlab, Inc., Atlanta, Ga.

Although we have demonstrated an overall efficient use of the reduced-carbon source (i.e., 1-butene), we sought a means of taking the olefinic dimer and converting it to a higher boiling material [e.g., $C_{16}$ compound(s)]. The latter could then be blended with little negative effect on the flash point of the fuel. Thus, treatment of 2-ethyl-1-hexene with concentrated sulfuric acid leads to rapid conversion to a complex mixture of monounsaturated $C_{16}$ alkenes (Scheme 2). The proton and carbon NMR spectral data for the product mixture are quite complicated (FIGS. 3 and 4); however, the GC-MS data (FIGS. 5-7) is consistent with an elution time that is expected for $C_{16}$ isomers, and most importantly, a molecular ion peak of 224 is observed for each peak in the GC-MS chromatogram, with very small amounts of 238 molecular ions ($C_{17}$ alkenes) indicated.

The mixture of $C_{16}$-alkene isomers has a measured density of about 0.80 g/mL that is similar to pure linear n-hexadecane (0.773 g/mL). One of the unique and useful features for these 1-butene derived fuels is the high degree of branching (100%) yet a good overall retention of fuel density. We note that although for jet fuels cetane rating is not specified nor directly related to any performance parameter, there is interest to further evaluate these fuels for their respective cetane and octane ratings. Extensive and regular ethyl branching is not typically found in fuel blends; therefore, an appropriate model for predicting a cetane rating is not presently available. Fuel density is an important parameter that contributes to meeting fuel performance requirements and may ultimately determine if a biojet version of JP-5/JP-8 can indeed meet or exceed mission critical Department of Defense (DoD) requirements.

Scheme 2

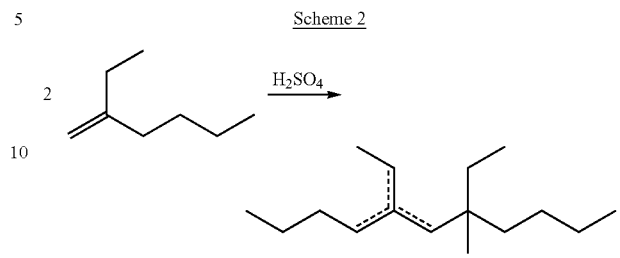

Experimental

General Methods.

All organometallic manipulations were carried out using standard Schlenk techniques under an atmosphere of purified nitrogen or in a glovebox. 1-butene (CP grade) was purchased from Specialty Gas Concepts, stirred over $CaH_2$, and degassed prior to use. MAO (10% in toluene) and $PtO_2$ were purchased from Aldrich and used as received. $Cp_2ZrCl_2$ was purchased from Strem and used as received. Butene oligomerization reactions were conducted in a 750 mL stainless steel Parr reactor fitted with a glass insert. $^1H$ and $^{13}C$ NMR spectra were collected on a Bruker Avance II 300 MHz spectrometer in $CDCl_3$ and referenced to the residual solvent peaks ($^1H$, _7.27; $^{13}C$, _77.16). Fuel samples were analyzed for viscosity (ASTM D445 at −20° C.), lubricity (ASTM D6069, HFRR), and flashpoint (ASTM D93) at Southwest Research Institute.

GC/MS Analysis Methods.

0.5 mg of oligomer mixture was dissolved in 1.0 mL of methylene chloride. 1 μL of sample was injected into an Agilent 6890 gas chromatography (GC) system equipped with a Restek RTX-5MS 30-meter column. The GC inlet temperature was 250° C., the initial column temperature was 40° C. held at 3 min, and the temperature was increased at 10° C./min up to a final temperature of 350° C. An Agilent mass selective detector 5973 system was used to identify the sample components.

Synthesis of Butene Oligomers (Method A).

Utilizing Schlenk techniques, $Cp_2ZrCl_2$ (70 mg, 0.24 mmol) was dissolved in MAO solution (16.5 mL, 25 mmol) to yield a pale yellow solution which was stirred at ambient temperature for 1 h. The resulting golden colored solution was then stripped of solvent under reduced pressure (0.1 mm Hg) to give a yellow solid. The flask was taken into a glovebox and the solid transferred to a bomb. The bomb was then removed from the glovebox and packed in dry ice. 1-butene (375 mL, 4.22 mol) was condensed into the bomb which was sealed, placed on a stir plate, allowed to warm to room temperature, and allowed to react for 16 h with stirring. A port on top of the bomb was opened (with a nitrogen purge) and this released a significant partial vacuum due to the complete conversion of butene to oligomers. The catalyst was quenched with distilled water (1 mL) and the mixture was stirred for 1 h. The top portion of the bomb was completely removed to reveal a white heterogeneous mixture smelling strongly of olefins. This mixture was filtered through a short plug of basic alumina (2 cm) and glass wool to yield 230 g (97%) of butene oligomers.

Synthesis of Butene Oligomers (Method B).

The activated catalyst solution was prepared as above. The solvent was removed under reduced pressure (0.1 mm Hg) and dry 3-methyl heptane (10 mL), was added to the flask with vigorous stirring to form a pale yellow slurry that was then transferred via a syringe into the bomb. The oligomerization reaction was then carried out as above. Yields were similar to Method A.

Hydrogenation of Butene Oligomers.

Butene oligomers (400 g) were placed in a 3-neck flask with a gas outlet. The solution was degassed and the atmosphere was replaced with nitrogen. $PtO_2$ (400 mg, 1.76 mmol) was added and the mixture was placed under a continuous hydrogen pressure of 2 psig. One of ordinary skill in the art will understand that butene oligomers may also readily be hydrogenated under pressure using nickel catalysts. The reaction could be conveniently monitored by NMR spectroscopy, but flocculation of the catalyst occurred upon completion of the reaction and was subsequently used to determine the end point. After 24 h the reaction mixture was filtered through glass wool to give a quantitative yield of colorless liquid.

Dimerization of 2-ethyl-1-hexene.

A flask was charged with sulfuric acid (98%, 0.3 mL) and 2-ethyl-1-hexene (4.45 g, 40 mmol) in that order. There was an initial exotherm upon mixing. The heterogenous mixture was allowed to react with stirring at ambient temperature for a period of 16 h. The colorless organic layer was separated and washed with aqueous $Na_2CO_3$ solutions (3×3 nit), followed by distilled water (3 mL) and analyzed by GC/MS, $^1H$ and $^{13}C$ NMR spectroscopy. Most of the peaks observed by GC/MS have molecular ion peaks of 224 and eluted in the range of 15-17 min, suggesting that primarily dimerization had taken place without a significant amount of cracking. The NMR spectra of the mixture were complex due to the formation of several isomers, yet the ratio of aliphatic protons to olefinic protons determined by NMR spectroscopy was consistent with an average formulation of $C_{16}H_{32}$ based on the assumption that primarily tri-substituted olefins were formed by the acid catalysis.

By tuning the catalyst and then using the dimer produced, we can bring the carbon use to about 95% or greater. This latter point will be particularly important in the future, where the source of raw materials (i.e., biomass/biofeedstock) is limited. Also noteworthy, the batch catalysis approach herein requires a minimal input of energy and hydrogen to make fuels that possess useful flash points, coldflow properties, and solution density/energy content. This new process affords a saturated hydrocarbon fuel that has a higher solution density and thus possesses a higher calculated power density (per volume) than similar fuels made by the GTL Fischer-Tropsch processes.

An aspect of the invention generally relates to processes including, activating a Group 4 metallocene pre-catalyst with methylaluminoxane in a suitable solvent, removing the solvent from the activated catalyst, mixing at least one aromatic solvent, without heteroatoms, with activated catalyst to form a solution, adding dried 1-butene to the solution, allowing contact of the activated catalyst with 1-butene in a gas tight vessel to form a first mixture of butene oligomers, removing by distillation the C8 dimer to produce a second mixture of butene oligomers, contacting of the second mixture of butene oligomers with a hydrogenation catalyst and hydrogen gas to create a third mixture of butene oligomers, and fractional distilling of the third mixture of butene oligomers to afford a high flash point turbine and diesel fuel.

In embodiments, the C8 dimer (2-ethyl-1-hexene) is placed in contact with concentrated sulfuric acid to form a heterogenous fourth mixture, stirring the fourth mixture to allow contact of reactants at ambient temperature until reaction is complete to form a reaction fifth mixture, separating the organic phase from the aqueous phase of the fifth mixture, and isolating butene $C_{16}$ oligomers from the organic phase. In other embodiments, the C8 dimer (2-ethyl-1-hexene) is placed in contact with concentrated sulfuric acid to form a heterogenous fourth mixture, stirring the fourth mixture to allow contact of reactants at temperatures from about 0-60° C. until reaction is complete to form a reaction fifth mixture, separating the organic phase from the aqueous phase of the fifth mixture, and isolating butene $C_{16}$ oligomers from the organic phase. In embodiments, the Group 4 metallocene catalyst is selected from the group consisting of at least one metal from titanium, zirconium, or hafnium.

In embodiments, at least one aromatic solvents is used having one aromatic ring and from 9 to 16 carbon atoms. In embodiments, the hydrogenation catalyst used has at least one metal taken from Group 10 of the periodic table. In embodiments, the hydrogen gas pressure is from about 10 psig to about 2000 psig. Embodiments further include contacting the C16 oligomers with a hydrogenation catalyst and hydrogen pressure to produce a mixture of C16 oligomers that are fully saturated with hydrogen. Other aspects of the invention generally relate to turbine and diesel fuels prepared by the processes above.

Another aspect of the invention generally relates to processes include, activating a Group 4 metallocene pre-catalyst with methylaluminoxane in a suitable solvent, removing the solvent from the activated catalyst, mixing at least one aromatic solvent, without heteroatoms, with activated catalyst to form a solution, adding dried 1-butene to the solution, contacting of the activated catalyst with 1-butene in a gas tight vessel to form a first mixture of butene oligomers, removing by distillation C8 dimers to produce a second mixture of butene oligomers, contacting of the second mixture of butene oligomers with a hydrogenation catalyst and hydrogen gas to create a third mixture of butene oligomers, contacting the C16 oligomers with a hydrogenation catalyst and hydrogen pressure to produce a fourth mixture of saturated C16 oligomers, adding the new mixture of C16 oligomers prepared above to the third mixture of butene oligomers to create a forth mixture of butene oligomers, and fractional distilling of the fourth mixture of butene oligomers to afford a high flash point turbine and diesel fuel.

In embodiments, the Group 4 metallocene catalyst is selected from the group consisting of at least one metal from titanium, zirconium, or hafnium. In embodiments, at least one aromatic solvents is used having one aromatic ring and from 9 to 16 carbon atoms. In embodiments, the hydrogenation catalyst used has at least one metal taken from Group 10 of the periodic table. In embodiments, the hydrogen gas pressure is from about 10 psig to about 2000 psig. In embodiments, the C8 dimer (2-ethyl-1-hexene) is placed in contact with concentrated sulfuric acid to form a heterogenous fourth mixture, and stirring the fourth mixture to allow contact of reactants at temperatures from about 0-60° C. until reaction is complete to form a reaction fifth mixture, and separating the organic phase from the aqueous phase of the fifth mixture, and isolating butene $C_{16}$ oligomers from the organic phase. Yet other aspects of the invention include turbine and diesel fuels prepared by the processes above.

While what are presently considered to be the most practical and preferred embodiments have been described, it is to be understood that the invention is not to be limited to the disclosed embodiments, but to the contrary, is intended to cover various modifications, embodiments, and equivalent processes included within the spirit of the invention as may be suggested by the teachings herein, which are set forth in the appended claims, and which scope is to be accorded the broadest interpretation so as to encompass all such modifications, embodiments, and equivalent processes.

What is claimed is:

1. A turbine and diesel fuel prepared by the process, comprising:
   activating a Group 4 metallocene pre-catalyst with methylaluminoxane in a suitable solvent, wherein said pre-catalyst is converted to an activated catalyst;
   removing said solvent from said activated catalyst;
   mixing at least one aromatic solvent, without heteroatoms, with said activated catalyst to form a solution;
   adding dried 1-butene to said solution;
   allowing contact of said activated catalyst with 1-butene in a gas tight vessel to form a first mixture of butene oligomers;
   removing by distillation using a $C_8$ dimer to produce a second mixture of butene oligomers;
   contacting of said second mixture of butene oligomers with a hydrogenation catalyst and hydrogen gas to create a third mixture of butene oligomers; and
   fractional distilling of said third mixture of butene oligomers to afford a turbine and diesel fuel.

2. The turbine and diesel fuels according to claim 1, wherein said $C_8$ dimer is (2-ethyl-1-hexene) and is placed in contact with concentrated sulfuric acid to form a heterogenous fourth mixture;
   stirring said fourth mixture to allow contact of reactants at ambient temperature until reaction is complete to form a reaction fifth mixture;
   separating an organic phase from the aqueous phase of said fifth mixture; and
   isolating butene $C_{16}$ oligomers from said organic phase.

3. The turbine and diesel fuels according to claim 1, wherein said $C_8$ dimer is (2-ethyl-1-hexene) and is placed in contact with concentrated sulfuric acid to form a heterogenous fourth mixture;
   stirring said fourth mixture to allow contact of reactants at temperatures from about 0-60° C. until reaction is complete to form a reaction fifth mixture;
   separating an organic phase from the aqueous phase of said fifth mixture; and
   isolating butene $C_{16}$ oligomers from said organic phase.

4. The turbine and diesel fuels according to claim 1, wherein said Group 4 metallocene pre-catalyst is selected from the group consisting of at least one metal from titanium, zirconium, or hafnium.

5. The turbine and diesel fuels according to claim 1, wherein said at least one aromatic solvents is used having one aromatic ring and from 9 to 16 carbon atoms.

6. The turbine and diesel fuels according to claim 1, wherein said hydrogenation catalyst used has at least one metal taken from Group 10 of the periodic table.

7. The turbine and diesel fuels according to claim 1, wherein said hydrogen gas has a pressure from about 10 psig to about 2000 psig.

8. The turbine and diesel fuels according to claim 7, further comprising contacting said $C_{16}$ oligomers with a hydrogenation catalyst and hydrogen pressure to produce a mixture of $C_{16}$ oligomers that are fully saturated with hydrogen.

9. A turbine and diesel fuel prepared by the process, comprising:
   activating a Group 4 metallocene pre-catalyst with methylaluminoxane in a suitable solvent, wherein said pre-catalyst is converted to an activated catalyst;
   removing said solvent from said activated catalyst;
   mixing at least one aromatic solvent, without heteroatoms, with said activated catalyst to form a solution;
   adding dried 1-butene to the solution;
   contacting of said activated catalyst with 1-butene in a gas tight vessel to form a first mixture of butene oligomers;
   removing by distillation $C_8$ dimers to produce a second mixture of butene oligomers;
   contacting of said second mixture of butene oligomers with a hydrogenation catalyst and hydrogen gas to create a third mixture of butene oligomers;
   contacting $C_{16}$ butene oligomers with a hydrogenation catalyst and hydrogen pressure to produce a fourth mixture of saturated $C_{16}$ butene oligomers;
   adding the new mixture of $C_{16}$ oligomers to the third mixture of butene oligomers to create a forth mixture of butene oligomers; and
   fractional distilling of the fourth mixture of butene oligomers to afford a turbine and diesel fuel.

10. The turbine and diesel fuels according to claim 9, wherein said Group 4 metallocene pre-catalyst is selected from the group consisting of at least one metal from titanium, zirconium, or hafnium.

11. The turbine and diesel fuels according to claim 9, wherein said at least one aromatic solvents is used having one aromatic ring and from 9 to 16 carbon atoms.

12. The turbine and diesel fuels according to claim 9, wherein said hydrogenation catalyst used has at least one metal taken from Group 10 of the periodic table.

13. The turbine and diesel fuels according to claim 9, wherein said hydrogen gas has a pressure from about 10 psig to about 2000 psig.

14. The turbine and diesel fuels according to claim 9, wherein said $C_8$ dimer is (2-ethyl-1-hexene) and is placed in contact with concentrated sulfuric acid to form a heterogenous fourth mixture;
   stirring said fourth mixture to allow contact of reactants at temperatures from about 0-60° C. until reaction is complete to form a reaction fifth mixture;
   separating the organic phase from the aqueous phase of said fifth mixture; and
   isolating butene $C_{16}$ oligomers from said organic phase.

* * * * *